US010138494B2

(12) United States Patent
Ko (10) Patent No.: US 10,138,494 B2
(45) Date of Patent: Nov. 27, 2018

(54) WHOLE EXPRESSED CELL AS ANTIGEN CARRIER, AND USE THEREOF IN PREPARING VACCINE OR DIAGNOSTIC AGENT, AND SCREENING MONOCLONAL ANTIBODIES

(71) Applicant: Formosa Biomedical Inc., Peitou, Changhua (TW)

(72) Inventor: Shun-Wen Ko, Changhua (TW)

(73) Assignee: FORMOSA BIOMEDICAL INC., Changhua (TW)

( * ) Notice: Subject to any disclaimer, the term of this patent is extended or adjusted under 35 U.S.C. 154(b) by 0 days.

(21) Appl. No.: 15/288,935

(22) Filed: Oct. 7, 2016

(65) Prior Publication Data
US 2018/0080042 A1 Mar. 22, 2018

(30) Foreign Application Priority Data
Oct. 8, 2015 (TW) .............................. 104133204 A (51) Int. Cl.
| | |
|---|---|
| *C12N 15/86* | (2006.01) |
| *C12N 15/87* | (2006.01) |
| *G01N 33/569* | (2006.01) |
| *G01N 33/577* | (2006.01) |
| *A61K 39/215* | (2006.01) |

(Continued)

(52) U.S. Cl.
CPC .............. *C12N 15/86* (2013.01); *A61K 39/12* (2013.01); *A61K 39/135* (2013.01); *A61K 39/215* (2013.01); *A61P 31/14* (2018.01); *A61P 31/20* (2018.01); *C07K 16/10* (2013.01); *C07K 16/1009* (2013.01); *C12N 15/87* (2013.01); *G01N 33/56983* (2013.01); *G01N 33/577* (2013.01); *A61K 2039/5156* (2013.01); *A61K 2039/545* (2013.01); *A61K 2039/552* (2013.01); *C12N 2710/24122* (2013.01); *C12N 2710/24134* (2013.01); *C12N 2710/24143* (2013.01); *C12N 2710/24152* (2013.01); *C12N 2710/24171* (2013.01); *C12N 2750/10034* (2013.01); *C12N 2750/10071* (2013.01); *C12N 2770/20034* (2013.01); *C12N 2770/20071* (2013.01); *C12N 2770/32134* (2013.01); *C12N 2770/32171* (2013.01); *G01N 2333/01* (2013.01); *G01N 2333/09* (2013.01); *G01N 2333/165* (2013.01); *G01N 2800/26* (2013.01)

(58) Field of Classification Search
None
See application file for complete search history.

(56) References Cited

U.S. PATENT DOCUMENTS

2008/0226669 A1* 9/2008 Roof ...................... A61K 39/04
424/201.1
2014/0335118 A1* 11/2014 Wang ............... G01N 33/56983
424/186.1

OTHER PUBLICATIONS

B. Moss (Science. Jun. 21, 1991; 252 (5013): 1662-1667).*
(Continued)

*Primary Examiner* — Shanon A. Foley
(74) *Attorney, Agent, or Firm* — Muncy, Geissler, Olds & Lowe, PC (57) ABSTRACT

A mammalian cell co-transfect with an expression plasmid comprising T7 promoter and an open reading frame (ORF) of target antigen, and a vT7 recombinant vaccinia virus expressing T7 polymerase. The entire antigen expressing cell is used as a carrier of the target antigen for preparing a vaccine or diagnostic agent, and screening monoclonal antibodies.

8 Claims, 4 Drawing Sheets

Specification includes a Sequence Listing.

(51) Int. Cl.
*A61K 39/12* (2006.01)
*A61K 39/135* (2006.01)
*C07K 16/10* (2006.01)
*A61P 31/20* (2006.01)
*A61P 31/14* (2006.01)
*A61K 39/00* (2006.01)

(56) References Cited

OTHER PUBLICATIONS

Bae et al. (Vaccine. 2003; 21: 4052-058).*
Sequence alignment of SEQ 3 with Geneseq database acc No. ADY59676 by Odenthal May 2005.*
Fuerst et al., "Eukaryotic transient-expression system based on recombinant vaccinia virus that synthesizes bacteriophage T7 RNA polymerase," Proc Natl. Acad. Sci., USA, vol. 83, pp. 8122-8126, Nov. 1986.
Lee et al., Pathology and Viral Distributions of the Porcinophilic Foot-And-Mouth Disease Virus Strain (O/Taiwan/97) in Experimentally Infected Pigs, Transboundary and Emerging Diseases, 56, Mar. 5, 2009, pp. 189-201.
Chang et al., "The Outbreak of Porcine Epidemic Diarrhea in Taiwan," Taiwan Veterinary Journal, vol. 40, No. 3, Sep. 22, 2014, pp. 115-121.
Strugnell et al., "Understanding Modern Vaccines: Perspectives in Vaccinology," Chapter 3: Vaccine antigens, vol. 1, Issue 1, 2011, pp. 61-88.
Ball, "High-Frequency Homologous Recombination in Vaccinia Virus DNA," Journal of Virology, Jun. 1987, pp. 1788-1795.

* cited by examiner

WHOLE EXPRESSED CELL AS ANTIGEN CARRIER, AND USE THEREOF IN PREPARING VACCINE OR DIAGNOSTIC AGENT, AND SCREENING MONOCLONAL ANTIBODIES

BACKGROUND OF THE INVENTION

Technical Field of the Invention

The present invention relates to a mammalian cell co-transfected with an expression plasmid comprising T7 promoter and an open reading frame (ORF) for target antigen, and a vT7 recombinant vaccinia virus expressing T7 polymerase. The entire antigen expressing cell is used as a carrier of the target antigen for preparing a vaccine or diagnostic agent, and screening monoclonal antibodies.

Background

The main component of a vaccine is an antigen, and the best antigen is usually an entire pathogen (Richard Strugnell et al, Understanding Modern Vaccines: Perspectives in Vaccinology, Chapter 3, Volume 1/Issue 1/61-88, 2011), such as foot-and mouth disease virus (FMDV), porcine epidemic diarrhea virus (PEDV), and so on. When some pathogens are difficult or impossible to be cultivated to a sufficient titer value for commercial production, or the antigens need to be produced under high biosafety norms (such as FMDV), it is necessary to produce such antigens by some biotechnologies.

However, virus can be divided into two general categories: enveloped or non-enveloped. Enveloped viruses, such as PEDV, can stimulate immune or be used as a vaccine antigen and they can completely bind to the surface protein of the cell membrane (envelope). As for non-enveloped viruses, such as FMDV, they can generate entire virus particles in the cell by self-reproduction. Therefore, viral antigens which can produce the best immune response should be closer to the original configurations or patterns of protein.

Comparing with the traditional viral antigen preparation, which is to cultivate the virus directly, the new generation of antigen preparation is to express and purify the antigenic protein after molecular cloning their genes. Since the objects infected by virus are higher eukaryotes, such as human, economic animals, pets, poultry, fish, shrimp, etc, their protein synthesis mechanisms differ greatly from prokaryotes. The quality of antigens and the prerequisite of their applications in vaccines, diagnostic reagents and screening monoclonal antibodies highly depend on the possibility of producing the protein almost equivalent to the target virus.

Thus, in order to produce immunogenic viral antigens, it has been tried to directly express the full-length open reading frame (ORF) of surface protein (for instance: PEDV surface proteins) in the cell by either adding a start codon ATG to the N-terminus or adding a stop codon TAA/TAG/TGA (such as foot and mouth disease virus VP1, VP2, VP3) to the C-terminus, and then antigen proteins with the same original characteristics as the virus will be prepared. The purpose of the present invention is to achieve the best antigen expression (in both quality and quantity).

SUMMARY OF INVENTION

Based on the above purposes, the invention provides an expression system for target antigen vector produced by co-transfection, comprising: (a) a expression plasmid containing T7 promoter and an open reading frame (ORF) of a target antigen; and a mammalian cell for carrying a vT7 recombinant vaccinia virus expressing T7 polymerase. The mammalian cell/antigen expresses an entire viral antigen with original structure, and can be used as a resource of the target antigen for preparing a vaccine or diagnostic agent, and screening monoclonal antibodies.

Accordingly, in one aspect, the present invention features an express system for the target antigen, which includes: (a) an expression plasmid comprising T7 promoter and an open reading frame (ORF) for target antigen protein; (b) a vT7 recombinant vaccinia virus expressing T7 polymerase; and (c) a mammalian cell.

In certain embodiments of the present invention, the antigen expression system is a mammalian cell, which expresses a whole virus or protein after co-transfection. In one embodiment, the mammalian cell is a Vero cell. In another embodiment, the open reading frame of the target antigen is linked to the downstream of the T7 promoter.

In one embodiment, the target antigen is a viral antigen. In one embodiment, the viral antigen is a surface protein of an enveloped virus. In one embodiment, the enveloped virus is a porcine epidemic diarrhea virus (PEDV). In another embodiment, the viral antigen is virus like particle (VLP) of anon-enveloped virus. In one embodiment, the enveloped virus is a Porcine Circovirus Type II (PCV2). In another embodiment, the target antigen is foot and mouth disease virus (FMDV) particles.

In another aspect, the present invention features a method of preparing the said antigen expressing animal cells, which comprises: infecting animal cells with the recombinant vaccinia virus carrying the T7 polymerase gene; co-transfecting the infected animal cells with an expression plasmid comprising T7 promoter and an open reading frame (ORF) of the target antigen, to obtain the animal cells for target antigen expression.

In one embodiment, the animal cell is a Vero cell. In another embodiment, the animal cell is a mammalian cell which can be infected by vaccinia virus.

In another embodiment, the present invention provides a vaccine composition, which comprises the said antigen expressing animal cell as an antigen carrier for directly immunizing animals.

In another embodiment, the present invention provides a vaccine composition for antibody screening, which comprises the said animal cells as antigen carriers.

In another embodiment, the present invention provides an antigen composition for screening monoclonal antibodies, which comprises the said animal cells as antigen carriers.

In another aspect, the present invention relates to a diagnostic kit to detect whether the animals are infected by the target virus, which comprise the said antigen expressing animal as the antigen carrier to determine whether antibodies against the target virus existing in the serum sample.

DETAILED DESCRIPTION OF THE INVENTION

Other features and advantages of the present invention will be further illustrated in the following examples, while these examples are described merely as an auxiliary, and they cannot limit the scope of the invention.

Example 1. Cloning of T7 Polymerase Gene

The full-length T7 polymerase gene is obtained from strains of E. coli BL21 (DE3) by PCR, and the promoter of vaccinia is introduced by using the following primers: the forward primer 3'-TTT GCGGCCG CTTTTTTTTT TTTTTTTTTT TGGCATATAA TAACATCGCT AAGAAC-5'(SEQ ID No. 1); and the reverse primer 3'-TTTGCGGCCG CTTACGCGAA CGCGAAGTCC-5' (SEQ ID No. 2). The resulting DNA was imported into TK1 and TKr of plastid pGS20 by PCR. Then, Vero cells were co-transfecting with the recombinant plasmid and a wild isolated strain of vaccinia virus (WR strain). After gene recombination and BrDu (Bromodeoxyuridine) screening (L. ANDREW BALL, J. Virol. 61: 1788-1795, 1987), recombinant vaccinia virus strains with T7 polymerase gene (2652 nucleotides, 883 a.a., as shown in SEQ ID No. 3) were cloned. And a pure vT7 strain, named $vT7_{FBI}$, was obtained after three times of plaque purification. The recombinant strain $vT7_{FBI}$ is deposited with CCTCC (China Center for Type Culture Collection), under Accession number V201550.

The property was confirmed by Co-transfect method, which contains the expression system controlled by the T7 promoter. The procedure is as follows: at first, $vT7_{FBI}$ Vero cells were infected with virus (0.1 MOI); and then the mixture of pT7-GFP/turbofect was added. The next day, the green fluorescence of cells can be observed directly under the fluorescence microscope, while the negative control group shows no fluorescence. Therefore, the ORF under the control of cell, $vT7_{FBI}$ and T7 promoter can be operated for the expression of a target protein.

Example 2. Preparation of the Cells which can Express Surface Protein PEDV

Figure 1:
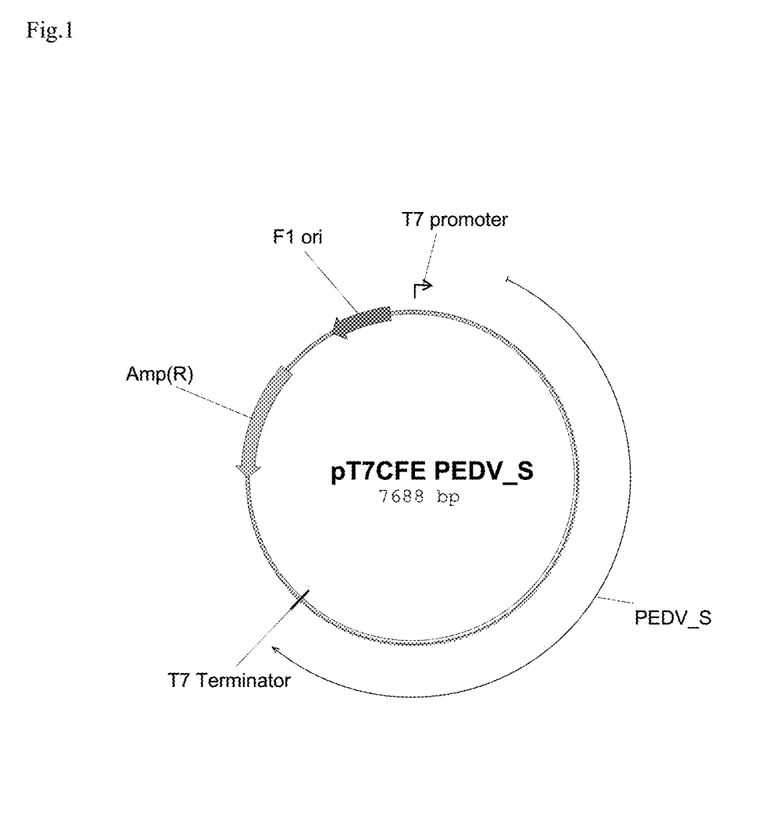
FIG. 1 shows the restriction map of the plasmid pT7CFE PEDV_TW_S.

The gene (4161 bp) of full-length Spike protein (a.a.: 1386) of PEDV strains separated in Changhua (Formosa Biomedical Inc., FBI, isolated from field, 2014 new variant PEDV strain, see M.-C. Deng et al., Taiwan Veterinary Journal, Vol. 40, No. 3: 115-121, 2014) were cloned by RT-PCR, and its cDNA sequence is shown in SEQ ID No. 4. Then, the cDNA was positioned downstream of the T7 promoter by PCR approach. And plastid pT7CFE PEDV_TW_S (shown in FIG. 1) was constructed and expressed by using T7 promoter.

The expression of cells can be achieved by using Vero cells as host cells, T7 recombinant vaccinia virus ($vT7_{FBI}$, 1 MOI), as well as plasmid pT7CFE PEDV_TW_S. After trypsinized, Vero cells were grown in a culture flask overnight until 70-80% full. Then, the medium was removed. The vT7 recombinant vaccinia prepared in example 1 was added at the ratio of 1 MOI and incubated at 37° C. for about 3 hours.

Preparation of the mixture of plasmid pT7CFE PEDV_TW_S and PEI. 10 mL of serum antibiotic phenol red free DMEM and 20 µg plasmid pT7CFE PEDV_TW_S DNA were placed in a 150-cm flask, then 20 µl PEI (Polysciences, Inc. Cat #23966 1 µg/µl) was added and mixed well. The resulting mixture was slowly added to the above Vero cells which have been infected with a recombinant vaccinia virus vT7. After mixing, the DMEM solution containing 2% serum was added and kept in an incubator containing 5% carbon dioxide at 37° C. for 24-36 hours. Then, the cells were fixed with 0.02% formaldehyde, and the amount of expression in the recombinant protein PEDV of Vero cells was measured.

Part of the cells was carried for immunofluorescence staining. After washing with PBS, anti-PEDV monoclonal antibody (Anti-PEDV S-M1-5, own preparation, prepared in a procedure as described in Example 7) was added in the sample, and incubated at room temperature for one hour. After the incubation, the sample was washed with PBS for three times. Then, FITC-conjugated rabbit anti-pig IgG antiserum (Biomedicals, FITC-conjugated rabbit fraction to swine IgG Cat #55824, 500-fold dilution in PBS) was added and reacted at room temperature for one hour. After the reaction, the sample was washed with PBS three times again. And the specific fluorescence of anti PEDV surface protein was observed under a fluorescent microscope. The results were shown in FIG. 2, and the fluorescence can be observed on most of the surface (more than 95%) of the cells.

PEDV Antibody Detection

Blood samples were heated at 56° C. for 30 minutes to remove serum complements. Two-fold serial dilution was performed as follow: 100 µL 2% FBS DMEM medium was added into the each well of a 96-well plate. The undiluted serum to be tested was placed in the column H of the 96-well plate, and each sample was added to two adjacent wells, and 100 µL medium was added to each well. The serum and 2% FBS DMEM medium in the wells in column H were stirred and thoroughly mixed by micropipettes, and then 100 µL of the resulting mixture was transferred to the wells in column G which was further sufficiently mixed with 2% FBS DMEM medium, and then 100 µL of the resulting mixture was transferred to the wells in column F, repeating the above steps until the serum sample was diluted twice in each transfer from column H to column A. Finally 100 µL mixed dilution was obtained from column A.

The PEDV virus was appropriately diluted by 2% FBS DMEM medium until the virus concentration was 100 $TCID_{50}$/50 µL (i.e. $2\times10^3$ $TCID_{50}$/mL). Then, 100 µL diluted standard virus solution was added to the each well of 96-well plate containing diluted serum samples, and the mixture was incubated in an incubator containing 5% $CO_2$ at 37° C. for one hour. Control groups were also selected for each experiment, which included cell control groups, positive serum control groups, serum control groups (for testing the cytotoxicity of serum), negative serum control groups and so on. As for cell control groups, 200 µL 2% FBS DMEM medium were added; for positive serum control groups, a known serum with determined neutralizing antibody titer could be taken as a positive control. The operation method for control groups is the same as the detecting method for serum samples as described previously. Finally, CPE (Cytopathic effect) was observed under the microscope after 5-7 days. Samples with no CPE indicate that neutralizing antibody responses exist.

Example 3. Preparation of Recombinant Carrier Cells with Expression of PCV2 (Porcine Circovirus Type 2; PCV2) ORF2

Figure 3:
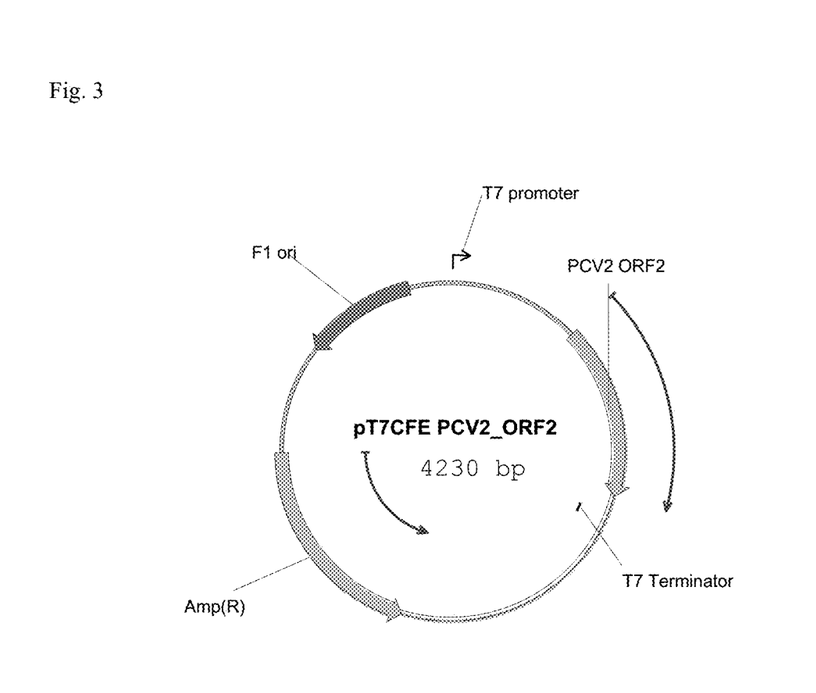
FIG. 3 shows the restriction map of the plasmid pT7CFE PCV2_ORF2.

The gene cloning was carried out by PCR, using the full length ORF2 (702 nucleotides, 233 a.a.) of porcine circovirus type II strains (FBI isolated from diseased piglets in the field) separated in Tainan as a template. And its cDNA sequence is shown in SEQ ID No. 5. Then, the cDNA was linked to the downstream of the T7 promoter by PCR approach. And the plasmid pT7CFE PCV2_ORF2 (as shown in FIG. 3) was constructed and expressed by using T7 promoter. The cell expression can be achieved by using Vero cells as host cells, T7 recombinant vaccinia virus (vT7$_{FBI}$, 1 MOI), as well as plasmid pT7CFE PCV2_ORF2. After typsinization, Vero cells were grown in the culture flask overnight until 70-80% comfluency. Then, the medium was removed. The vT7$_{FBI}$ recombinant vaccinia prepared in example 1 was added to the Vero cells at the ratio of 1 MOI (Multiplicity of infection) and incubated at 37° C. for 3 hours.

Preparation of the mixture of plasmid pT7CFE PCV2_ORF2 and PEI (Polyethylenimine). 10 mL of serum antibiotic phenol red free DMEM and 20 μg plasmid pT7CFE PCV2_ORF2 DNA were placed in a 150 cm flask, then 20 μl PEI (Polysciences, Inc. Cat #23966 1 μg/μl) was added and mixed well. The resulting mixture was slowly added to the prepared Vero cells which have been infected with a recombinant vaccinia virus vT7$_{FBI}$. After mixing, the DMEM solution containing 2% serum was added and kept in an incubator containing 5% carbon dioxide at 37° C. for 24-36 hours. Then, the cells were fixed with 0.02% formaldehyde, and the amount of recombinant PCV2 ORF2 protein expressed in the Vero cells was measured.

A part of the cells was taken for immunofluorescence staining. After the recombinant Vero cells (2×10$^4$ cells/well) were washed with PBS, Swine anti-PCV2 antibody L36 (antiserum of SPF pigs infected with PCV2, own preparation) was added and reacted at room temperature for one hour. Next, the sample was washed with PBS three times. Then, FITC-conjugated goat anti-pig IgG antiserum (MP Biomedicals, FITC-conjugated goat IgG fraction to mouse immunoglobulins IgG IgA, IgM, Cat number 55499, 500-fold dilution in PBS) was added at room temperature and reacted for one hour. After the reaction, the sample was washed with PBS three times again. And the specific fluorescence of anti-PCV2 ORF2 surface protein can be observed under a fluorescent microscope. And the amount of cell expression is generally over 95%

The resulting entire recombinant Vero cells could be used as antigen for immunization, and about 10$^6$ cells can be formulated in one dose. Oil adjuvant or aluminum gel adjuvant could be used for immunization of SPF pigs. After three immune injections, the serum was taken to measure antibody titer by PCV2 IFA antibody assay as described in following examples.

Example 4. Preparation of Antigen Plate PCV2 ORF2

A 96-well plate with each well containing 80% confluent of the Vero cells (2×10$^4$ cells) was prepared, and 0.1 MOI of recombinant virus vT7 (vT7$_{FBI}$) which was prepared as described in the Example 1 was added. Plasmid pT7CFE PCV2_ORF2 DNA was extracted by maxi-prep and quantified. The plasmid pT7CFE PCV2_ORF2 DNA and PEI were mixed evenly. The DNA/Turbofect® (Thermo Fisher Scientific Inc) were mixed and added to the cell plates. After transfection for 24 hours, supernatant was removed, and 80% acetone was added to fix. After removing acetone and drying, the PCV2 ORF2 antigen coating plate with the recombinant cells as antigen carrier was obtained. Finally, the antigen coating plate was package and stored at −80° C.

Figure 4A:
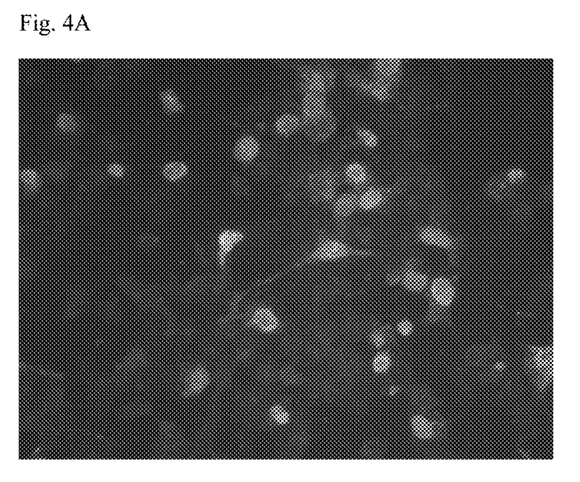
FIGS. 4A and 4B show the specific fluorescence when Vero cells express PCV2 protein under the microscope: positive as shown in FIG. 4A and negative as shown in FIG. 4B.
Figure 4B:
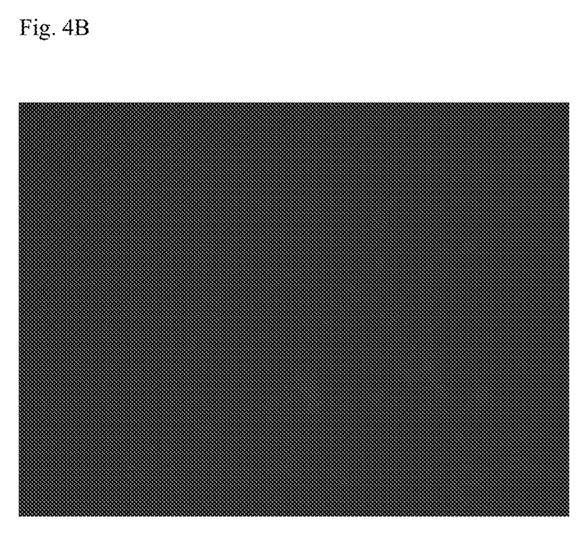

The serum sample was added to each well of a 96-well plate. After two-fold serial dilution with PBS (initial dilution is 50×), the mixture was transferred to the PCV2 ORF2 antigen coating plate prepared as described above, and kept at room temperature for one hour, then followed by washing with PBS three times. FITC-conjugated goat anti-pig IgG antiserum (MP Biomedicals, FITC-conjugated goat IgG fraction to mouse immunoglobulins IgG IgA, IgM, Cat number 55499, 500-fold dilution in PBS) was added and kept at room temperature for one hour, then washed with PBS three times. Fluorescent antibody titers were observed under the microscope. The standard positive result was shown as in FIG. 4A, while the negative one was shown as in FIG. 4B. The standard positive fluorescence for PCV2 was shown as in FIG. 4A, which indicates that most fluoresce was presented in the cell nucleus, and this was in accordance with the characteristics of this protein. The visible light image in the same area was shown in FIG. 4B.

Figure 2:
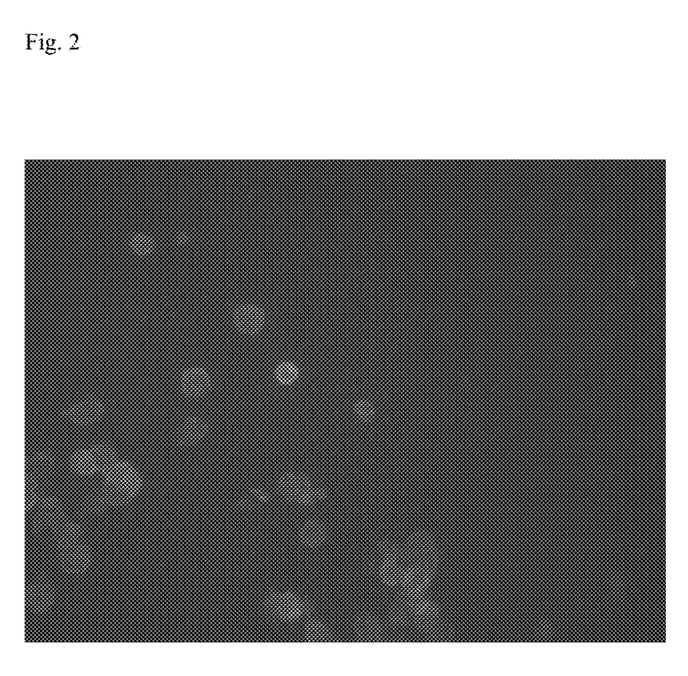
FIG. 2 shows the specific fluorescence when Vero cells express PEDV surface protein by fluorescent immunoassay and fluorescence microscopy analysis in Example 2.

Example 5. Immunization Experiments by Using the Full-Length Cells with Expressed PEDV Surface Protein as Antigens After trypsinization, Vero cells were grown in a cell culture flask overnight until 70-80% confluency. Then, the medium was removed. And the mixture of plasmid pT7CFE PEDV_TW_S and PEI was added. In a 150 cm flask, 10 mL DMEM (serum antibiotic phenol red free), 20 μg plasmid pT7CFE PEDV_TW_S DNA and 20 μl PEI (Poysciences, Inc. Cat #23966 1 μg/μl) was added. After mixing slowly, the mixture was added to the Vero cells which had infected with recombinant vT7 vaccinia virus vT7$_{FBI}$. After mixing well, DMEM containing 2% serum was added and cultured for 24-36 hours. Then, the cells were fixed with 0.02% formaldehyde immediately, and the expression level was measured. Generally, the cell expression rate is over 95% (FIG. 2).

The prepared entire Vero cells can be used as antigen for immunization, about 10$^6$/cell can be formulated in one dose. An oil adjuvant or aluminum gel adjuvant can be used for immunization of SPF pigs. After the procedures of immune injection as listed in Table 1, the antibody titer of serum samples were measured by PEDV neutralizing antibody assay.

TABLE 1

| | | Neutralizing antibody response in PEDV antigen immunized SPF pigs | | | | | | |
|---|---|---|---|---|---|---|---|---|
| SPF pig | Immune dose | 0 week | 2 weeks | Boosting 4 weeks | 6 weeks | 8 weeks | Boosting 12 weeks | 14 weeks |
| 557-01 | 1 ml | <4 | <4 | <4 | 16 | 8 | 16 | 128 |
| 557-03 | 1 ml | <4 | <4 | <4 | 8 | 16 | 8 | 64 |
| 557-05 | 2 ml | <4 | <4 | 4 | 16 | 16 | 16 | 64 |
| 557-07 | 2 ml | <4 | <4 | 4 | 32 | 32 | 16 | 128 |

The results showed that the best injection dosage for the immunization of SPF pig with the Vero cell expressed PEDV surface protein of the present invention is 2 ml/dose, and requiring at least two injections.

Example 6. Preparation of Specific Viral Pathogen Antigen Plate

According to the preparation method of PCV2 ORF2 antigen plate for detecting the PCV2 IFA antibody titers as mentioned in Example 4, the antigen plate for detecting desired antibodies could be directly produced on a conventional antigen detection article, such as a 96-well plate, by using animal cells as the host cells, co-transfected with the vT7 recombinant vaccinia virus (1MOI) and an expression plasmid containing DNA fragments encoding the desired antigen placed downstream of T7 promoter.

Example 7. Screening of the Anti-PEDV Monoclonal Antibodies

Following the preparation method described in Example 2, the cells expressing PEDV surface protein ($10^6$ cells/mouse) were obtained and directly injected to immunize mice (Balb/C). Then, after the antibody titer was raised over 100×, spleen cells of the immunized mice were separated and fused to SP2 cells. The screening method of antigen is the same as described in Example 4, and the cells expressing PEDV surface proteins were cultured in a 96-well plate, which could be used as antigen plate of screening monoclonal antibodies. As a result, a monoclonal antibody with positive reaction for PEDV surface protein was obtained, which was designated as S-M1-5.

Example 8. Preparation of Recombinant Carrier Cells Expressing FMDV Virus Particles Coat proteins of FMD virus can self-assemble into particles to form empty shells. Moreover, the empty shelled particles produced from FMD virus infected cells are non-contagious, and have the same antigenicity and immunogenicity as the intact virus. The preparing method used in this example is similar to the previously described method. Briefly, the polypeptide of FMD virus was first digested into small subunits, and then the start codon ATG was added at the N-terminus of the amino acid sequence of each subunit; and stop codons TAA/TAG/TGA were added at the C-terminus of the amino acid sequence of each subunit; the corresponding protein fragments, such as subunit protein 3A, 3B, 3C, 3AB or 3ABC of foot and mouth disease virus, were expressed by a recombinant cell of the present invention under the control of T7 promoter.

After expressions of VP4 (1A), VP2 (1B), VP3 (1C) of FMDV O/97 (GenBank: AF026168.2 see S. -H. Lee, et al., Transboundary and Emerging Diseases. 56: 189-201, 2009) and staining with 11 monoclonal antibodies from Department of Veterinary Medicine at National Taiwan University, only one antibody show negative responds. As for the expression system of P1 full-length (VP4231), only monoclonal antibody Q10E-3, K12F-1, and N10E-1 appeared positive results, but others were negative, indicating that only P1 cannot produce complete virus particles. The full-length DNA containing the P1 main antigen VP231 expressed after co-transfecting cells with 3ABC or 3C could reacted with most of the monoclonal antibodies. The result is similar to the co-transfection of P1 with 3ABC or 3C, and showed a stronger fluorescence response, indicating that the former could produce more corresponding antigen (viroid) (as shown in Table 2).

TABLE 2

The reaction of the monoclonal antibodies with the various combinations or linkages of P1 or VP231 with 3ABC or 3C

| Monoclonal antibody | VP231 + 3ABC | VP231 + 3C | VP231 | VP231_2A_3ABC | P1_2A + 3C | P1_2A | P1_2A + 3ABC | P1_2A_3ABC |
|---|---|---|---|---|---|---|---|---|
| K12F-1 | ++++ | ++++ | +++ | ++++ | ++++ | ++++ | ++++ | +++ |
| N8F-12 | + | + | − | + | + | − | + | + |
| I9B-2 | ++++ | +++ | − | ++++ | + | − | + | + |
| Q10E-3 | ++++ | +++ | ++ | ++++ | +++ | +++ | +++ | ++++ |
| S10F-1 | ++++ | +++ | − | ++++ | − | − | ++ | ++++ |
| S12G-6 | ++++ | +++ | − | ++++ | +++ | − | ++ | +++ |
| N10E-1 | ++++ | +++ | + | ++++ | + | + | +++ | ++++ |
| M10B-9 | ++++ | ++++ | − | ++++ | +++ | − | +++ | + |
| Q2B-20 | ++++ | ++++ | − | ++++ | + | − | ++ | + |
| T2B-5 | ++++ | ++++ | − | ++++ | +++ | − | ++ | + |
| S11B-20 | + | − | − | + | − | − | − | − |

As a result, both P1_2A_3ABC P1_2A combined from P12A and 3ABC, or P1_2A_3ABC combined from VP231_2A and 3ABC VP2312A, can exhibit fluorescence properties as the two DNA co-transfected cells, indicating that they may be expressed and remained their original functions in the host cell. In addition to the full-length P1 (or only VP231), the complete FMDV virus structure also need the cooperating action of 2A and 3ABC, or 3C. The best combination of DNA must be the linkage to P1_2A_3ABC or VP231_2A_3ABC, and the former showed the better response than the latter, which demonstrates that VP4 does not play a decisive role in the assembly of intact virus particles. Obviously, the expression system of the present invention can produce intact and antigenic virus particles in the absence of FMDV infection, so they can be used as the raw materials for the production of foot and mouth disease vaccine after ultrafiltration. Moreover, the results of the present examples also demonstrate the expression system of the present invention can be used directly for the analysis of a monoclonal antibody to the corresponding antigen.

The invention claimed is:

1. An animal cell expression system for a target antigen of porcine epidemic diarrhea virus (PEDV), comprising an animal cell co-transfected with:

(a) an expression plasmid containing a T7 promoter and an open reading frame (ORF) for a FEDV viral antigen protein or its fragment; and (b) a vT7 recombinant vaccinia virus (vT7$_{FBI}$) expressing T7 polymerase comprising a coding nucleotide sequence of SEQ ID No.3.

2. The animal cell expression system of claim 1, wherein the target antigen is a surface protein of a porcine epidemic diarrhea virus (PEDV).

3. The animal cell expression system of claim 2, wherein the porcine epidemic diarrhea virus is a new variant strain of porcine epidemic diarrhea virus (PEDV).

4. The animal cell expression system of claim 1, wherein the open reading frame (ORF) of the PEDV viral antigen or its fragment is fused to the downstream of the T7 promoter.

5. A vaccine composition, comprising the animal cell expression system of claim 1 and an immunologically acceptable carrier or adjuvant, wherein the animal cell expression system is used as an antigen carrier to directly immunize animals.

6. A method for preparing the animal cell expression system of claim 1, comprising:
   (1) infecting an animal cell with a recombinant vaccinia virus carrying a T7 polymerase gene of SEQ ID NO.3; and
   (2) co-transfecting the infected animal cell with an expression plasmid comprising a T7 promoter and an open reading frame (ORF) of the PEDV viral antigen protein or a fragment of the PEDV viral antigen protein to obtain an animal cell expressing the antigen.

7. The method of claim 6, wherein the animal cell is a Vero cell.

8. The method of claim 6, wherein the animal cell is a mammalian cell which is susceptible to an infection of vaccinia virus.

\* \* \* \* \*

SEQUENCE LISTING

<160> NUMBER OF SEQ ID NOS: 5

<210> SEQ ID NO 1
<211> LENGTH: 56
<212> TYPE: DNA
<213> ORGANISM: artificial sequence
<220> FEATURE:
<223> OTHER INFORMATION: synthetic primer

<400> SEQUENCE: 1
tttgcggccg cttttttttt tttttttttt tggcatataa taacatcgct aagaac        56

<210> SEQ ID NO 2
<211> LENGTH: 30
<212> TYPE: DNA
<213> ORGANISM: artificial sequence
<220> FEATURE:
<223> OTHER INFORMATION: synthetic primer

<400> SEQUENCE: 2
tttgcggccg cttacgcgaa cgcgaagtcc        30

<210> SEQ ID NO 3
<211> LENGTH: 2651
<212> TYPE: DNA
<213> ORGANISM: artificial sequence
<220> FEATURE:
<223> OTHER INFORMATION: T7 RNA Polymerase

<400> SEQUENCE: 3
atgaacacga ttaacatcgc taagaacgac ttctctgaca tcgaactggc tgctatcccg        60
ttcaacactc tggctgacca ttacggtgag cgtttagctc gcaacagtt ggcccttgag       120
catgagtctt acgagatggg tgaagcacgc ttccgcaaga tgtttgagcg tcaacttaaa       180
gctggtgagg ttgcggataa cgctgccgcc aagcctctca tcactaccct actccctaag       240
atgattgcac gcatcaacga ctggtttgag gaagtgaaag ctaagcgcgg caagcgcccg       300
acagccttcc agttcctgca agaaatcaag ccggaagccg tagcgtacat caccattaag       360
accactctgg cttgcctaac cagtgctgac aatacaaccg ttcaggctgt agcaagcgca       420
atcggtcggg ccattgagga cgaggctcgc ttcggtcgta ccgtgaccct tgaagctaag       480
cacttcaaga aaaacgttga ggaacaactc aacaagcgcg tagggcacgt ctacaagaaa       540
gcatttatgc aagttgtcga ggctgacatg ctctctaagg gtctactcgg tggcgaggcg       600
tggtcttcgt ggcataagga agactctatt catgtaggag tacgctgcat cgagatgctc       660
attgagtcaa ccggaatggt tagcttacac cgccaaaatg ctggcgtagt aggtcaagac       720
tctgagacta tcgaactcgc acctgaatac gctgaggcta tcgcaacccg tgcaggtgcg       780
ctggctggca tctctccgat gttccaacct tgcgtagttc ctcctaagcc gtggactggc       840
attactggtg gtggctattg ggctaacggt cgtcgtcctc tggcgctggt gcgtactcac       900
agtaagaaag cactgatgcg ctacgaagac gtttacatgc ctgaggtgta caaagcgatt       960
aacattgcgc aaaacaccgc atggaaaatc aacaagaaag tcctagcggt cgccaacgta      1020
atcaccaagt ggaagcattg tccggtcgag gacatccctg cgattgagcg tgaagaactc      1080
ccgatgaaac cggaagacat cgacatgaat cctgaggctc tcaccgcgtg gaaacgtgct      1140
gccgctgctg tgtaccgcaa ggacaaggct cgcaagtctc gccgtatcag ccttgagttc      1200
atgcttgagc aagccaataa gtttgctaac cataggcca tctggttccc ttacaacatg      1260
gactggcgcg gtcgtgttta cgctgtgtca atgttcaacc cgcaaggtaa cgatatgacc      1320

```
aaaggactgc ttacgctggc gaaaggtaaa ccaatcggta aggaaggtta ctactggctg      1380
aaaatccacg gtgcaaactg tgcgggtgtc gataaggttc cgttccctga gcgcatcaag      1440
ttcattgagg aaaaccacga aacatcatg gcttgcgcta agtctccact ggagaacact       1500
tggtgggctg agcaagattc tccgttctgc ttccttgcgt tctgctttga gtacgctggg      1560
gtacagcacc acggcctgag ctataactgc tcccttccgc tggcgtttga cgggtcttgc      1620
tctggcatcc agcacttctc cgcgatgctc cgagatgagg taggtggtcg cgcggttaac      1680
ttgcttccta gtgaaaccgt tcaggacatc tacgggattg ttgctaagaa agtcaacgag      1740
attctacaag cagacgcaat caatgggacc gataacgaag tagttaccgt gaccgatgag      1800
aacactggtg aaatctctga gaaagtcaag ctgggcacta aggcactggc tggtcaatgg      1860
ctggcttacg tgttactcg cagtgtgact aagcgttcag tcatgacgct ggcttacggg       1920
tccaaagagt tcggcttccg tcaacaagtg ctggaagata ccattcagcc agctattgat      1980
tccggcaagg gtctgatgtt cactcagccg aatcaggctg ctggatacat ggctaagctg      2040
atttgggaat ctgtgagcgt gacggtggta gctgcggttg aagcaatgaa ctggcttaag      2100
tctgctgcta agctgctggc tgctgaggtc aaagataaga agactggaga gattcttcgc      2160
aagcgttgcg ctgtgcattg ggtaactcct gatggtttcc ctgtgtggca ggaatacaag      2220
aagcctattc agacgcgctt gaacctgatg ttcctcggtc agttccgctt acagcctacc      2280
attaacacca caaagatag cgagattgat gcacacaaac aggagtctgg tatcgctcct      2340
aactttgtac acagccaaga cggtagccac cttcgtaaga ctgtagtgtg ggcacacgag      2400
aagtacggaa tcgagtcttt tgcactgatt cacgactcct tcggtaccat tccggctgac      2460
gctgcgaact tgttcaaagc agtgcgcgaa actatggttg acacatatga gtcttgtgat      2520
gtactggctg atttctacga ccagttcgct gaccagttgc acgagtctca attggacaaa      2580
atgccagcac ttccggctaa aggtaacttg aacctccgtg acatcttaga gtcggacttc      2640
gcgttcgcgt a                                                          2651

<210> SEQ ID NO 4
<211> LENGTH: 4161
<212> TYPE: DNA
<213> ORGANISM: Porcine epidemic diarrhea virus

<400> SEQUENCE: 4
atgaggtctt taatttactt ctggttgctc ttaccagtac tttcaacact tagcctacca       60
caagatgtca ccaggtgctc agctaacact aattttaggc ggttctttc aaaatttaat      120 gttcaggcgc ctgcagttgt tgtactgggc ggttatctac ctattggtga aaaccagggt      180
gtcaattcaa cttggtactg tgctggccaa catccaactg ctagtggcgt tcatggtatc      240
tttgttagcc atattagagg tggtcatggc tttgagattg gcatttcgca agagcctttt      300 gacccctagtg ttaccagct ttatttacat aaggctacta acggtaacac taatgctact      360
gcgcgactgc gcatttgcca gtttcctagc attaaaacat gggcccccac tgctaataat      420
gatgttacaa caggtcgtaa ttgcctattt aacaaagcca tcccagctca tatgagtgaa      480
catagtgttg tcggcataac atgggataat atcgtgtca ctgtcttttc tgacaagatc       540
tattattttt attttaaaaa tgattggtcc cgtgttgcga caaagtgtta caacagtgga     600
ggttgtgcta tgcaatatgt ttacgaaccc acctattaca tgcttaatgt tactagtgct     660
ggtgaggatg gtatttctta tcaaccctgt acagctaatt gcattggtta tgctgccaat      720
gtatttgcta ctgagcccaa tggccacata ccagaaggtt ttagttttaa taattggttt      780
```

-continued

```
cttttgtcca atgattccac tttggtgcat ggtaaggtgg tttccaacca accattgttg      840
gtcaattgtc ttttggccat tcctaagatt tatggactag ccaattttt ctccttaat       900
caaacgatcg atggtgtttg taatggagct gctgtgcagc gtgcaccaga ggctctgagg     960
tttaatatta atgacacctc tgtcattctt gctgaaggct caattgtact tcatactgct    1020
ttaggaacaa attttcttt tgtttgcagt aattcctcaa atcctcactt agccaccttc     1080
gccatacctt tgggtgctac ccaagtaccc tattattgtt ttcttaaagt ggatacttac    1140
aactccactg tttataaact cttggctgtt ttacctccaa ccgtcaggga aattgtcatc    1200
accaagtatg gtgatgttta tgtcaatggg tttggatact tgcatctcgg tttgttggat    1260
gctgtcacaa ttaatttcac tggtcatggc actgacgatg atgtttctgg tttttggacc    1320
atagcatcga ctaatttcgt tgatgcactc atcgaagttc aaggaaccgc cattcagcgt    1380
attctttatt gtgatgatcc tgttagccaa ctcaagtgtt ctcaggttgc ttttgacctt    1440
gacgatggtt tttaccctat ttcttctaga aaccttctga gtcatgaaca gccaatttct    1500
tttgttactc tgccatcatt taatgatcat tcttttgtta acattactgt atctgcttcc    1560
tttggtggtc atagtggtgc caaccttatt gcatctgaca ctactatcaa tgggtttagt    1620
tctttctgtg ttgacactaa acaatttacc atttcactgt tttataacgt tacaaacagt    1680
tatggttatg tgtctaaatc acaggacagt aattgccctt tcaccttgca atctgttaat    1740
gattacctgt cttttagcaa attttgtgtt tccaccagcc ttttggctag tgcctgtacc    1800
atagatcttt ttggttaccc tgagtttggt agtggtgtta agtttacgtc cctttacttt    1860
caattcacaa agggtgagtt gattactggc acgcctaaac cacttgaagg tgtcacggac    1920
gtttctttta tgactctgga tgtgtgtacc aagtatacta tctatggctt aaaggtgag    1980
ggtatcatta cccttacaaa ttctagcttt tggcaggtg tttattacac atctgattct    2040
ggacagttgt tagcctttaa gaatgtcact agtggtgctg tttattctgt tacgccatgt    2100
tcttttttcag agcaggctgc atatgttgat gatgatatag tgggtgttat ttctagtttg    2160
tctagctcca cttttaacag tactagggag ttgcctggtt tcttctacca ttctaatgat    2220
ggctctaatt gtacagagcc tgtgttggtg tatagtaaca taggtgttg taaatctggc    2280
agtattggct acgtcccatc tcagtctggc caagtcaaga ttgcacccac ggttactggg    2340
aatattagta ttcccaccaa ctttagtatg agtattagga cagaatattt acagcttta    2400
aacacgcctg ttagtgttga ttgtgccaca tatgtttgta atggtaactc tcgttgtaaa    2460
caattactca cccagtacac tgcagcatgt aagaccatag agtcagcatt acaactcagc    2520
gctaggcttg agtctgttga agttaactct atgcttacta tttctgaaga ggctctacag    2580
ttagctacca ttagttcgtt taatggtgat ggatataatt ttactaatgt gctgggtgtt    2640
tctgtgtatg atcctgcaag tggcagggtg gtacaaaaaa ggtctttta tgaagacctg    2700
cttttaata aagtggttac taatggcctt ggtactgttg atgaagacta taagcgctgt    2760
tctaatggtc gctctgtggc agatctagtc tgtgcacagt attactctgg gtcatggta    2820
ctacctggtg ttgttgacgc tgagaagctt cacatgtata gtgcgtctct catcggtggt    2880
atggtgctag gaggttttac ttctgcagcg gcattgcctt ttagctatgc tgttcaagct    2940
agactcaatt atcttgctct acagacggat gttctacagc ggaaccagca attgcttgct    3000
gagtcttta actctgctat tggtaatata acttcagcct tgagagtgt taaagaggct    3060
attagtcaaa cttccaaggg tttgaacact gtggctcatg cgcttactaa ggttcaagag    3120
gttgttaact cgcagggtgc agctttgact caacttaccg tacagctgca acacaacttc    3180
```

```
caagccattt ctagttctat tgatgacatt tactctcgac tggacattct ttcagccgat    3240
gttcaggttg accgtctcat caccggcaga ttatcagcac ttaatgcttt tgttgctcaa    3300
accctcacta agtatactga ggttcaggct agcaggaagt tagcacagca aaaggttaat    3360
gagtgcgtta aatcgcaatc tcagcgttat ggttttttgtg gtggtgatgg cgagcacatt    3420
ttctctctgg tacaggcagc acctcagggc ctgctgtttt tacatacagt acttgtaccg    3480
agtgattttg tagatgttat tgccatcgct ggcttatgcg ttaacgatga aattgccttg    3540
actctacgtg agcctggctt agtcttgttt acgcatgaac ttcaaaatca tactgcgacg    3600
gaatattttg tttcatcgcg acgtatgttt gaacctagaa aacctaccgt tagtgattt     3660
gttcaaattg agagttgtgt ggtcacctat gtcaatttga ctagagacca actaccagat    3720
gtaatcccag attacatcga tgttaacaaa acacttgatg agattttagc ttctctgccc    3780
aatagaactg gtccaagtct tcctttagat gttttttaatg ccacttatct taatctcact    3840
ggtgaaattg cagatttaga gcagcgttca gagtctctcc gtaatactac agaggagctc    3900
caaagtctta tatataatat caacaacaca ctagttgacc ttgagtggct caaccgagtt    3960
gagacatata tcaagtggcc gtggtgggtt tggttgatta ttttcattgt tctcatctttt   4020
gttgtgtcat tactagtgtt ctgctgcatt tccacgggtt gttgtggatg ctgcggctgc    4080
tgctgtgctt gtttctcagg ttgttgtagg ggtcctagac ttcaaccta cgaagttttt    4140
gaaaaggtcc acgtgcagtg a                                               4161

<210> SEQ ID NO 5
<211> LENGTH: 702
<212> TYPE: DNA
<213> ORGANISM: Porcine Circovirus Type II
<220> FEATURE:
<223> OTHER INFORMATION: ORF2

<400> SEQUENCE: 5
atgacgtatc caaggaggcg tttccgcaga cgaagacacc gcccccgcag ccatcttggc     60
cagatcctcc gccgccgccc ctggctcgtc caccccgcc accgttaccg ctggagaagg     120
aaaaatggca tcttcaacac ccgcctctcc cgcaccttcg gatatactgt caaggctacc    180
acagtcagaa cgccctcctg ggcggtggac atgatgagat ttaatattaa cgactttgtt    240
cccccgggag ggggggaccaa caaaatctct ataccctttg aatactacag aataagaaag    300
gttaaggttg aattctggcc ctgctcccca atcacccagg gtgacagggg agtgggctcc    360
actgctgtta ttctagatga taacttttgta actaaggcca cagccctaac ctatgacccc    420
tatgtaaact actcctcccg ccatacaatc ccccaaccct tctcctacca ctcccggtac    480
tttacccca aacctgtcct tgattccact attgattact ccaaccaaa caacaaaagg    540
aatcagcttt ggctgaggct acaaacctcg gcaaatgtgg accacgtagg cctcggcact    600
gcgttcgaaa acagtaaata cgaccaagac tacaatatcc gtgtaactat gtatgtacaa    660
ttcagagaat ttaatcttaa agaccccca cttaaaccct ag                        702
```